(12) United States Patent
Delaney, Jr. et al.

(10) Patent No.: US 10,111,986 B2
(45) Date of Patent: Oct. 30, 2018

(54) PRODUCTION OF IN SITU CROSSLINKABLE POLYISOBUTYLENE-POLYURETHANE NANOFIBERS AND COATINGS

(71) Applicant: Cardiac Pacemakers, Inc., St. Paul, MN (US)

(72) Inventors: Joseph T. Delaney, Jr., Minneapolis, MN (US); Niraj Gurung, Sauk Rapids, MN (US); David R. Wulfman, Minneapolis, MN (US); Adegbola O. Adenusi, Burnsville, MN (US); Patrick Willoughby, Shoreview, MN (US); Adeniyi O. Aremu, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 45 days.

(21) Appl. No.: 15/293,583

(22) Filed: Oct. 14, 2016

(65) Prior Publication Data
US 2017/0106124 A1  Apr. 20, 2017

Related U.S. Application Data

(60) Provisional application No. 62/243,057, filed on Oct. 17, 2015.

(51) Int. Cl.
*A61L 31/06* (2006.01)
*A61L 31/10* (2006.01)
(Continued)

(52) U.S. Cl.
CPC ............. *A61L 31/06* (2013.01); *A61L 29/085* (2013.01); *A61L 31/10* (2013.01); *A61N 1/05* (2013.01);
(Continued)

(58) Field of Classification Search
CPC .......... C08L 23/22; C08L 53/00; C08L 75/04; C08G 18/12; C08G 18/3206;
(Continued)

(56) References Cited

U.S. PATENT DOCUMENTS 4,743,509 A * 5/1988 Vladimiro ................ B27D 1/00
                                                   144/348
5,243,011 A * 9/1993 Panandiker ............ C08G 18/10
                                                   252/182.21
(Continued)

FOREIGN PATENT DOCUMENTS

WO    2013078139 A1    5/2013
WO    2016171975 A1    10/2016

OTHER PUBLICATIONS

Cozzens, David, et al. "Electrospinning of Biostable Polyisobutylene-Based Thermoplastic Polyurethanes." Journal of Polymer Science, Part B: Polymer Physics, 51:452-459.

(Continued)

*Primary Examiner* — Thao T Tran
(74) *Attorney, Agent, or Firm* — Faegre Baker Daniels LLP (57) ABSTRACT

A method for making a device including a polyisobutylene-polyurethane block copolymer. The method includes polymerizing a polyisobutylene diol, a diisocyanate, and a chain extender within a solvent system to form a polyisobutylene-polyurethane block copolymer solution, depositing the polyisobutylene-polyurethane block copolymer solution onto at least a portion of the device, and evaporating the solvent system from the deposited polyisobutylene-polyurethane block copolymer solution.

19 Claims, 4 Drawing Sheets

(51) Int. Cl.
  *A61N 1/05*     (2006.01)
  *C08G 81/02*    (2006.01)
  *A61L 29/08*    (2006.01)
  *C08G 18/66*    (2006.01)
  *C08G 18/76*    (2006.01)
  *C08G 18/12*    (2006.01)
  *C08G 18/24*    (2006.01)
  *C08G 18/32*    (2006.01)

(52) U.S. Cl.
  CPC ............. *C08G 18/12* (2013.01); *C08G 18/24* (2013.01); *C08G 18/3206* (2013.01); *C08G 18/6674* (2013.01); *C08G 18/7671* (2013.01); *C08G 81/024* (2013.01); *A61L 2420/02* (2013.01); *A61N 1/056* (2013.01); *A61N 1/0507* (2013.01); *A61N 1/0534* (2013.01); *A61N 1/0541* (2013.01); *A61N 1/0543* (2013.01); *A61N 1/0551* (2013.01)

(58) Field of Classification Search
  CPC ........ C08G 81/025; C08J 3/09; A61L 29/085; A61L 31/06; A61L 31/10; A61L 2420/02; A61N 1/05
  USPC .............................. 607/116; 528/48, 65, 85
  See application file for complete search history.

(56) References Cited

U.S. PATENT DOCUMENTS

| | | | | |
|---|---|---|---|---|
| 5,428,123 | A * | 6/1995 | Ward | ..................... A61L 27/18 |
| | | | | 210/500.21 |
| 7,715,922 | B1 | 5/2010 | Tan | |
| 2003/0236513 | A1* | 12/2003 | Schwarz | ................. A61L 27/34 |
| | | | | 604/890.1 |
| 2010/0023104 | A1* | 1/2010 | Desai | ..................... A61L 27/18 |
| | | | | 607/119 |
| 2011/0054581 | A1 | 3/2011 | Desai et al. | |
| 2013/0131765 | A1 | 5/2013 | Polkinghorne et al. | |

OTHER PUBLICATIONS

Cozzens, David, et al. "Surface Characterization and Protein Interactions of Segmented Polyisobutylene-Based Thermoplastic Polyurethanes." Langmuir, 27:14160-14168, 2011.

Hansen, Charles M. Hansen Solubility Parameters: A User's Handbook, 2nd ed. New York, CRC Press, Taylor & Francis Group, 2007, 546 pages.

International Search Report and Written Opinion issued in PCT/US2016/056972, dated Feb. 3, 2017, 11 pages.

* cited by examiner

PRODUCTION OF IN SITU CROSSLINKABLE POLYISOBUTYLENE-POLYURETHANE NANOFIBERS AND COATINGS

CROSS-REFERENCE TO RELATED APPLICATION

This application claims priority to Provisional Application No. 62/243,057, filed Oct. 17, 2015, which is herein incorporated by reference in its entirety.

TECHNICAL FIELD

The present invention relates to medical devices and methods for manufacturing medical devices. More specifically, the invention relates to methods for making medical devices and medical devices including a layer of polyisobutylene-polyurethane block copolymer.

BACKGROUND

Polymeric materials are widely used in the field of implantable medical devices. For example, polymeric materials such as silicone rubber, polyurethane, and fluoropolymers are used as coating and/or insulating materials for medical leads, stents, and other devices.

Incorporating polymeric materials into implantable medical devices may be done by a variety of methods, depending on the specific application. In some applications, for example, for implantable lead bodies, the polymeric material may be extruded at a temperature sufficient to cause the polymeric material to flow, but not high enough to cause the polymeric material to break down. That is, the material that forms the lead after the extrusion and cooling has largely the same structure as the original polymeric material.

In other applications, it may be desirable to employ a solvent-based deposition process to incorporate a layer of the polymeric material into an implantable medical device. Solvent-based deposition processes include electrospraying, electrospinning, spray coating, dip coating, and force spinning. Essential to all solvent-based deposition processing of polymeric materials is that the polymeric material be in solution while retaining the basic structure of the polymeric material. In some cases, the very properties of strength and chemical resistance that characterize some polymeric materials also make it difficult to manufacture the polymeric material and to form solutions of the polymeric material.

Block copolymers are polymeric materials made of alternating sections of polymerized monomers. A polyisobutylene-polyurethane block copolymer is a polymeric material with many unique and desirable physical and mechanical properties, including thermal stability, chemical resistance, biocompatibility, and gas impermeability, among others. However, these physical characteristics may also make both the manufacturing and the solvent-based deposition processing of the polyisobutylene-polyurethane block copolymer difficult and time consuming. Improvements are needed in the manufacturing and solvent-based deposition processing of the polyisobutylene-polyurethane block copolymer.

SUMMARY

Example 1 is a method for making a device including a polyisobutylene-polyurethane block copolymer. The method includes polymerizing a polyisobutylene diol, a diisocyanate, and a chain extender within a solvent system to form a polyisobutylene-polyurethane block copolymer solution, depositing the polyisobutylene-polyurethane block copolymer solution onto at least a portion of the device, and evaporating the solvent system from the deposited polyisobutylene-polyurethane block copolymer solution.

In Example 2, the method of Example 1, wherein polymerizing further includes a polyether diol within the solvent system to form the polyisobutylene-polyurethane block copolymer solution.

In Example 3, the method of either of Examples 1 or 2, wherein evaporating the solvent system includes evaporating a first portion of the solvent system while depositing the polyisobutylene-polyurethane block copolymer solution, and evaporating a second portion of the solvent system following deposition of the deposited polyisobutylene-polyurethane block copolymer solution.

In Example 4, the method of Example 3, wherein allophonate crosslinks form within the polyisobutylene-polyurethane block copolymer during evaporation of the second portion of the solvent system.

In Example 5, the method of any of Examples 1-4, wherein the polymerization continues after deposition of the polyisobutylene-polyurethane block copolymer during evaporation of the solvent system.

In Example 6, the method of any of Examples 1-5, wherein the solvent system consists of one or more solvent components, and the one or more solvent components do not include hydroxyl groups, acids, acid halides, primary amines, secondary amines, primary amides, or secondary amides.

In Example 7, the method of any of Examples 1-6, wherein the solvent system includes 2,6-dimethylpyridine.

In Example 8, the method of any of Examples 1-7, wherein the solvent system includes benzaldehyde and a solvent component selected from the group consisting of 1,3-dioxolane, 1,4-dioxane, glycerol triacetate, ethyl 3-ethoxypropionate, tetrahydrofuran, dimethyl sulfoxide, diabasic esters, tetramethylene sulfone, and methyl phenylacetate.

In Example 9, the method of any of Examples 1-8, wherein depositing includes at least one of solvent casting, spray coating, or dip coating the polyisobutylene-polyurethane block copolymer solution onto the device.

In Example 10, the method of any of Examples 1-8, wherein the solvent system includes a solvent component having a polar Hansen Solubility Parameter of at least about 5.0 $MPa^{0.5}$ and a hydrogen bonding Hansen Solubility Parameter of at least about 4.4 $MPa^{0.5}$, or at least one solvent component having a polar Hansen Solubility Parameter of at least about 5.0 $MPa^{0.5}$ and at least one other solvent component having a hydrogen bonding Hansen Solubility Parameter of at least about 4.4 $MPa^{0.5}$.

In Example 11, the method of Example 10, wherein depositing includes at least one of electrospinning and electrospraying the polyisobutylene-polyurethane block copolymer solution onto the device.

In Example 12, the method of any of Examples 1-11, wherein a Hansen Solubility Parameter Distance Relative Energy Difference between the polyisobutylene-polyurethane block copolymer and the solvent system is less than about 1.

In Example 13, a device including a polyisobutylene-polyurethane block copolymer and made according to any of the methods of Examples 1-12, the copolymer including a plurality of linear polyisobutylene-polyurethane block copolymer segments; and a plurality of allophonate crosslinks between the linear polyisobutylene-polyurethane block copolymer segments.

In Example 14, the device of Example 13, wherein the copolymer is a thermoset polymer.

In Example 15, the device of either of Examples 13-14, wherein the device is an implantable medical device.

Example 16 is a method for making an implantable medical device including a polyisobutylene-polyurethane block copolymer. The method includes polymerizing a polyisobutylene diol, a diisocyanate, a chain extender, and optionally a polyether diol, within a solvent system to form a polyisobutylene-polyurethane block copolymer solution, depositing the polyisobutylene-polyurethane block copolymer solution onto at least a portion of the implantable medical device, and evaporating the solvent system from the deposited polyisobutylene-polyurethane block copolymer solution.

In Example 17, the method of Example 16, wherein evaporating the solvent system includes evaporating a first portion of the solvent system while depositing the polyisobutylene-polyurethane block copolymer solution, and evaporating a second portion of the solvent system following deposition of the deposited polyisobutylene-polyurethane block copolymer solution.

In Example 18, the method of Example 17, wherein allophonate crosslinks form within the polyisobutylene-polyurethane block copolymer during evaporation of the second portion of the solvent system.

In Example 19, the method of any of Examples 16-18, wherein the polymerization continues after deposition of the polyisobutylene-polyurethane block copolymer during evaporation of the solvent system.

In Example 20, the method of any of Examples 16-19, wherein the solvent system consists of one or more solvent components, wherein the one or more solvent components have boiling points less than about 350° C., relative evaporation rates greater than about 0.01, and vapor pressures greater than about 0.5 mm Hg.

In Example 21, the method of any of Examples 16-20, wherein the solvent system consists of one or more solvent components, and the one or more solvent components do not include hydroxyl groups, acids, acid halides, primary amines, secondary amines, primary amides, or secondary amides.

In Example 22, the method of any of Examples 16-21, wherein the solvent system includes 2,6-dimethylpyridine.

In Example 23, the method of Example 22, wherein the solvent system consists of 2,6-dimethylpyridine.

In Example 24, the method of any of Examples 16-21, wherein the solvent system includes benzaldehyde and a solvent component selected from the group consisting of 1,3-dioxolane, 1,4-dioxane, glycerol triacetate, ethyl 3-ethoxypropionate, tetrahydrofuran, dimethyl sulfoxide, diabasic esters, tetramethylene sulfone, and methyl phenylacetate.

In Example 25, the method of any of Examples 16-21, wherein the solvent system includes benzaldehyde, 1,4-dioxane, and a solvent component selected from the group consisting of caprolactone (epsilon), dimethyl sulfoxide, tetramethylene sulfone, propylene carbonate, gamma-butyrolactone, and N-methyl-2-pyrrolidone.

In Example 26, the method of any of Examples 16-25, wherein the polymerizing the polyisobutylene diol, the diisocyanate, the chain extender, and optionally the polyether diol, within the solvent system includes adding a tin catalyst to the solvent system.

In Example 27, the method of any of Examples 16-26, wherein depositing includes at least one of solvent casting, spray coating, or dip coating the polyisobutylene-polyurethane block copolymer solution onto the implantable medical device.

In Example 28, the method of Examples 16-26, wherein the solvent system includes a solvent component having a polar Hansen Solubility Parameter of at least about 5.0 $MPa^{0.5}$ and a hydrogen bonding Hansen Solubility Parameter of at least about 4.4 $MPa^{0.5}$, or at least one solvent component having a polar Hansen Solubility Parameter of at least about 5.0 $MPa^{0.5}$ and at least one other solvent component having a hydrogen bonding Hansen Solubility Parameter of at least about 4.4 $MPa^{0.5}$.

In Example 29, the method of Example 28, wherein depositing includes at least one of electrospinning and electrospraying the polyisobutylene-polyurethane block copolymer solution onto the implantable medical device.

In Example 30, the method of any of Examples 16-29, wherein the diisocyanate is 4,4'-methylenediphenyl diisocyanate, the chain extender is 1,4-butanediol, and the optional the polyether diol is polytetramethylene oxide diol.

In Example 31, the method of any of Examples 16-30, wherein a Hansen Solubility Parameter Distance Relative Energy Difference between the polyisobutylene-polyurethane block copolymer and the solvent system is less than about 1.

Example 32 is an implantable medical device including a polyisobutylene-polyurethane block copolymer. The copolymer includes a plurality of linear polyisobutylene-polyurethane block copolymer segments and a plurality of allophonate crosslinks between the linear polyisobutylene-polyurethane block copolymer segments.

In Example 33, the device of Example 32, wherein the copolymer is a thermoset polymer.

In Example 34, the device of either of Examples 32 or 33, wherein the implantable medical device is medical lead and the polyisobutylene-polyurethane block copolymer is in the form of a plurality of electrospun fibers on a surface of the medical lead.

In Example 35, the device of either of Examples 32 or 33, wherein the polyisobutylene-polyurethane block copolymer is in the form of a sprayed coating on at least a portion of a surface of the device.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Historically, polyisobutylene-polyurethane block copolymer (PIB-PUR) may be manufactured, or polymerized, in a first solvent, for example, toluene, and then dried under a vacuum or nitrogen blanket to evaporate as much toluene as possible from the PIB-PUR. Once the first solvent evaporates, polymerization ceases. Drying the PIB-PUR may take weeks due to the excellent diffusion barrier characteristics of PIB-PUR. Once enough of the toluene is evaporated from the PIB-PUR, the PIB-PUR may be dissolved in a second solvent, for example, pyridine, for deposition by a solvent-based deposition process. PIB-PUR will not continue to polymerize in the second solvent. Bringing the PIB-PUR into solution may take an additional several days because of the excellent chemical resistance of PIB-PUR.

In embodiments of the present invention, the polymerization to form the PIB-PUR, and the subsequent solvent-based deposition process to deposit the PIB-PUR on a medical device, are both performed using the same solvent system, as described below. The use of the same solvent system from polymerization through deposition eliminates the need for the long process steps of drying the PIB-PUR, and then bringing it back into solution for deposition by a solvent-based process. In embodiments, the entire process from polymerization through deposition may be completed in a single day.

Figure 1:
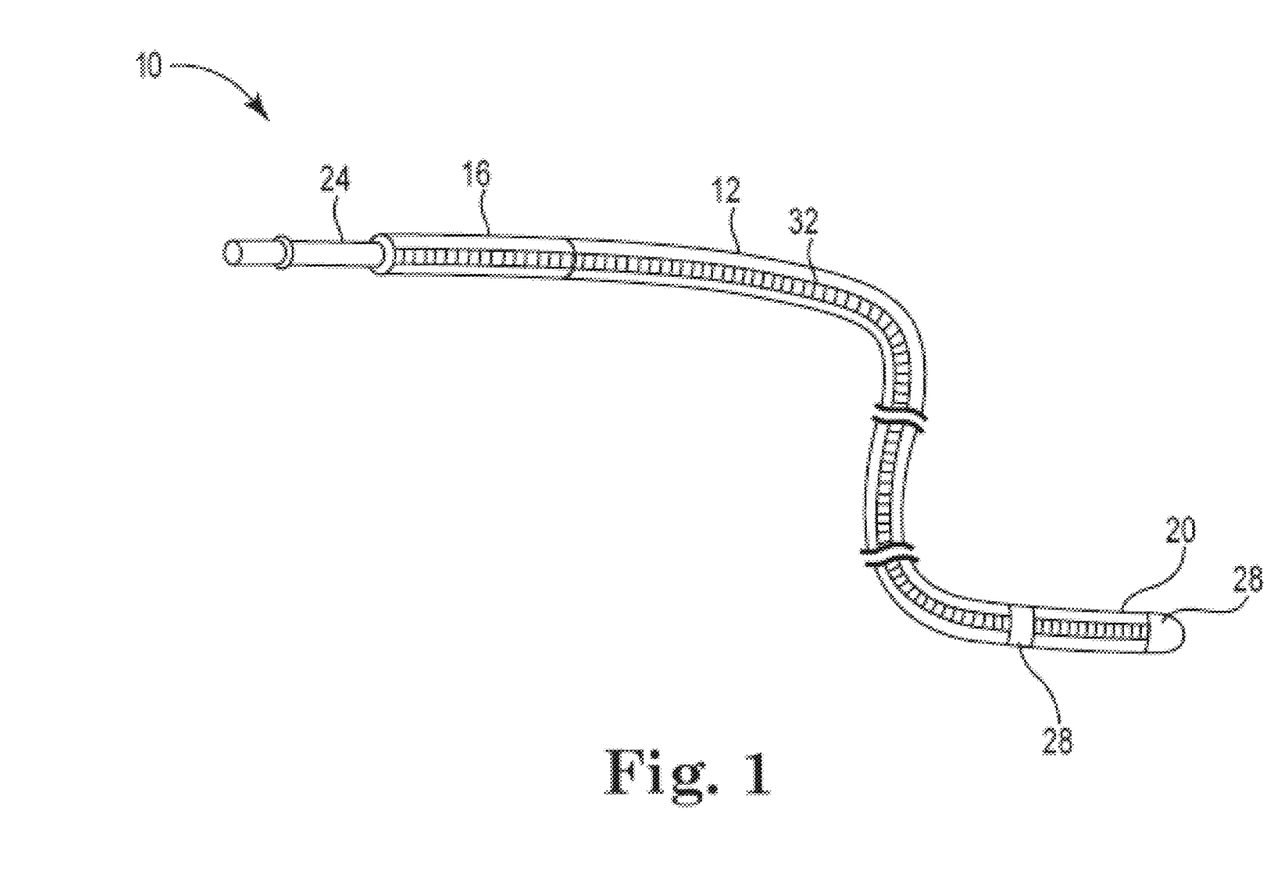
FIG. 1 is a schematic view of an implantable medical device according to embodiments of the present invention.

FIG. 1 provides an illustrative but non-limiting example of a medical application using an exemplary implantable medical device. The application and location are illustrative only, as implantable medical devices incorporating embodiments of the present invention may be used in a variety of anatomical locations and for a variety of additional purposes.

FIG. 1 is a partial cross-sectional view of a medical electrical lead 10, in accordance with various embodiments of the present disclosure. According to some embodiments, the medical electrical lead 10 can be configured for implantation within a patient's heart. According to other embodiments, the medical electrical lead 10 is configured for implantation within a patient's neurovascular regions. In yet another embodiment, the lead 10 can be a lead for a cochlear implant. The medical electrical lead 10 includes an elongated, insulative lead body 12 extending from a proximal end 16 to a distal end 20. The proximal end 16 is configured to be operatively connected to a pulse generator via a connector 24. At least one conductor 32 extends from the connector 24 at the proximal end 16 of the lead 10 to one or more electrodes 28 at the distal end 20 of the lead 10. The conductor 32 can be a coiled or cable conductor. According to some embodiments where multiple conductors are employed, the lead can include a combination of coiled and cable conductors. When a coiled conductor is employed, according to some embodiments, the conductor can have either a co-radial or a co-axial configuration.

The medical electrical lead 10 can be unipolar, bipolar, or multi-polar depending upon the type of therapy to be delivered. In embodiments of the present disclosure employing multiple electrodes 28 and multiple conductors 32, each conductor 32 is adapted to be connected to an individual electrode 28 in a one-to-one manner allowing each electrode 28 to be individually addressable. Additionally, the lead body 12 can include one or more lumens adapted to receive a guiding element such as a guide wire or a stylet for delivery of the lead 10 to a target location within a patient's heart.

The electrodes 28 can have any electrode configuration as is known in the art. According to one embodiment of the present disclosure, at least one electrode can be a ring or partial ring electrode. According to another embodiment, at least one electrode 28 is a shocking coil. According to yet another embodiment of the present disclosure, at least one electrode 28 includes an exposed electrode portion and an insulated electrode portion. In some embodiments, a combination of electrode configurations can be used. The electrodes 28 can be coated with or formed from platinum, stainless steel, titanium, tantalum, palladium, MP35N, other similar conductive material, alloys of any of the foregoing including platinum-iridium alloys, and other combinations of the foregoing including clad metal layers or multiple metal materials.

Figure 2A:
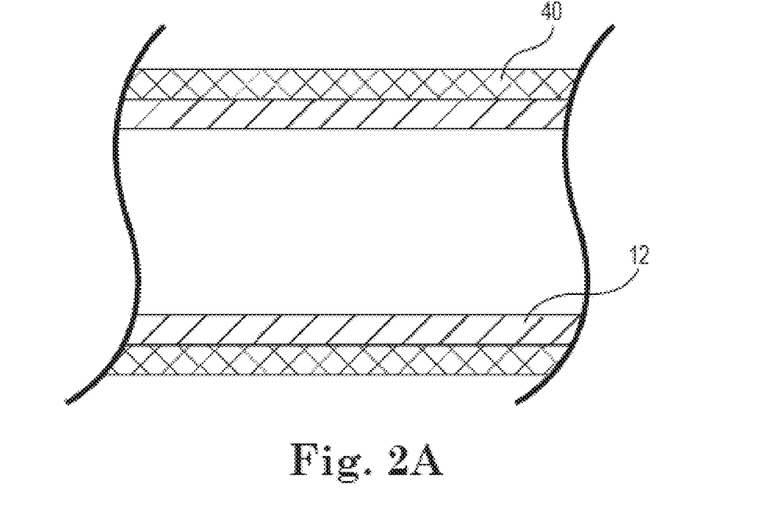
FIGS. 2A and 2B are schematic longitudinal cross-sections of portions of the implantable medical device of FIG. 1.
Figure 2B:
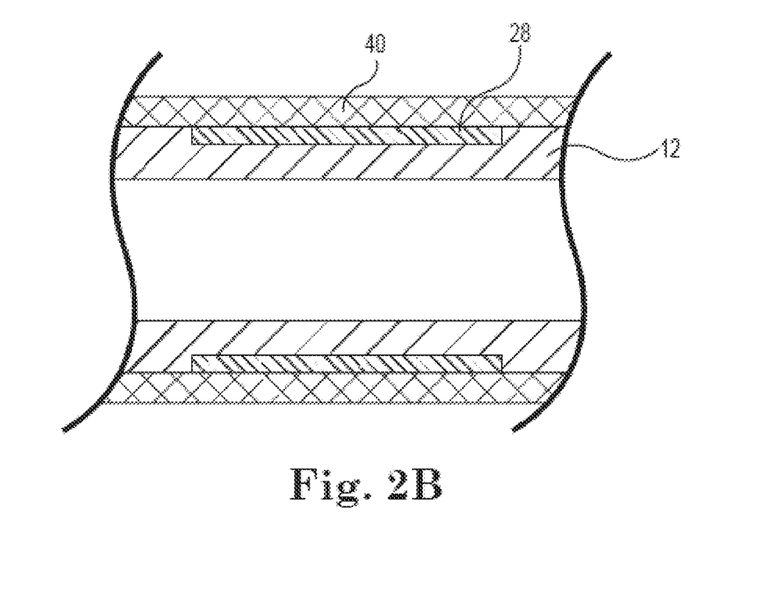

FIGS. 2A and 2B are schematic longitudinal cross-sectional views of the lead 10 of FIG. 1, in which internal structure has been removed for clarity. As shown in FIGS. 2A and 2B, the lead 10 includes a PIB-PUR layer 40 that is deposited over various parts of the insulative lead body 12. FIGS. 2A and 2B provide illustrative but non-limiting examples of regions of the lead 10 that may include the PIB-PUR layer 40.

FIG. 2A shows the PIB-PUR layer 40 disposed over a portion of the insulative lead body 12. The illustrated portion of the insulative lead body 12 may be adjacent an electrode such as the electrode 28, or it may be spaced apart from the electrodes. In contrast, FIG. 2B illustrates the PIB-PUR layer 40 disposed over the electrode 28. While the PIB-PUR layer 40 is illustrated as covering all of the electrode 28, in some embodiments the PIB-PUR layer 40 covers only a small portion of the electrode 28, a substantial portion of the electrode 28, or an intervening fraction of the electrode 28. In the embodiment shown in FIGS. 2A and 2B, the PIB-PUR layer 40 may be porous to allow electrical contact between the electrode 28 and tissues at the target location within the patient's heart.

In embodiments, a polyisobutylene diol, a diisocyanate, a chain extender, and optionally, a polyether diol may be polymerized within a solvent system to form a PIB-PUR solution. In some embodiments, the polyisobutylene diol may be a telechelic polyisobutylene diol. The use of the telechelic polyisobutylene diol produces a plurality of linear PIB-PUR segments. In some embodiments, the telechelic polyisobutylene diol may be saturated. Suitable diisocyanates may include 4,4'-methylenediphenyl diisocyanate (MDI), 2,4- and/or 2,6-toluene diisocyanate (TDI), 1,5-naphthalene diisocyanate (NDI), para-phenylene diisocyanate, 3,3'-tolidene-4,4'-diisocyanate, 3,3'-dimethyl-diphenylmethane-4,4'-diisocyanate, 1,6-hexamethylene diisocyanate (HDI), 4,4'-dicyclohexylmethane diisocyanate, 3-isocyanatomethyl-3,5,5-trimethylcyclohexyl isocyanate (isophorone diisocyanate or IPDI), cyclohexyl diisocyanate, and 2,2,4-trimethyl-1,6-hexamethylene diisocyanate (TMDI). Suitable chain extenders may include ethylene glycol (1,2-ethane diol), 1,4-butanediol, and 1,6-hexanediol. Suitable optional polyether diols may include polytetramethylene oxide diol (PTMO diol), polyhexamethylene oxide diol (PHMO diol), polyoctamethylene oxide diol, and polydecamethylene oxide diol. In some embodiments, the polymerization may occur in presence of a catalyst added to the solvent system. Suitable catalysts may include tin(II) 2-ethylhexanoate.

Solvent systems in accordance with embodiments may include a single solvent component, or a plurality of solvent components. Suitable solvent systems are able to maintain the PIB-PUR in solution, may not interfere with the polymerization process, and are sufficiently volatile to evaporate from the PIB-PUR solution under conditions that will not damage the PIB-PUR. In addition, for use in solvent-based deposition processes employing electric fields to control the deposition of the PIB-PUR solution, such as electrospinning and electrospraying, suitable solvent systems may also have polarity and hydrogen bonding levels sufficient to support interaction between the PIB-PUR solution and the electric fields.

Solvent systems in accordance with embodiments are able to maintain the PIB-PUR in solution. Hansen Solubility Parameters (HSPs) may be used to predict whether a material may dissolve in another. HSPs consist of three parameters representing forces acting between molecules of a substance: dispersion forces, polar intermolecular forces, and hydrogen bonding forces (see Charles M. Hansen, *Hansen Solubility Parameters: A User's Handbook* (CRC Press, 2d ed. 2007)). The three HSPs define a three-dimensional Hansen space. The three HSPs of a material are coordinates in the Hansen space. Thus, the HSPs of a material, such as a single solvent component or a polymer, determine the relative position of the material in the Hansen space. The HSPs of a mixture of a plurality of solvent components are a volume-weighted combination of the HSPs of the individual solvent components making up the mixture. Thus, a mixture of a plurality of solvent components also has a relative position in Hansen space. A Hansen Solubility Parameter Distance (Ra) is a distance in Hansen space between any two materials. The Ra may be determined from Equation 1 below:

$$Ra = \sqrt{4(\delta_{d2}-\delta_{d1})^2 + (\delta_{p2}-\delta_{p1})^2 + (\delta_{h2}-\delta_{h1})^2}$$ Eq. 1 where $\delta_{d1}$, $\delta_{p1}$, and $\delta_{h1}$ are the dispersion, polar, and hydrogen bonding HSPs, respectively, of one of the two materials; and $\delta_{d2}$, $\delta_{p2}$, and $\delta_{h2}$ are the dispersion, polar and hydrogen bonding HSPs of the other of two materials. The values of the HSPs for a particular solvent component or polymer may be determined empirically or may be found in published tables.

An interaction radius ($R_0$) may be determined for a material to be dissolved. $R_0$ is a distance in Hansen space within which any solvent component (or solvent mixture) is likely to form a solution with the material. The ratio of Ra to $R_0$ is known as a Relative Energy Difference (RED) and is a dimensionless number. For a material and a solvent component (or plurality of solvent components) having RED value greater than 1, the material and solvent component may not be sufficiently similar in their HSPs to form a solution. Conversely, for a material and a solvent (or plurality of solvent components) having RED value less than 1, the material and solvent component may be sufficiently similar in their HSPs that the material is likely to form a solution with the solvent component. Thus, the RED may predict whether a material is likely to form a solution with the solvent component (or plurality of solvent components).

In some embodiments of the present disclosure, the HSPs and the $R_0$ for PIB-PUR have been determined empirically. For PIB-PUR the dispersion HSP is about 19.3 MPa$^{0.5}$, the polar HSP is about 9.3 MPa$^{0.5}$, and the hydrogen bonding HSP is about 10.5 MPa$^{0.5}$. For PIB-PUR, the $R_0$ is about 5.9.

The HSPs for various solvents may be found in, for example, Charles M. Hansen, *Hansen Solubility Parameters: A User's Handbook* (CRC Press, 2d ed. 2007) incorporated herein by reference in its entirety.

In some embodiments, the solvent system may have an RED with respect to the PIB-PUR of less than about 1 to maintain the PIB-PUR in solution. For example, a solvent system consisting of 2,6-dimethylpyridine has a dispersion HSP of about 19.0 MPa$^{0.5}$, a polar HSP of about 8.9 MPa$^{0.5}$, and a hydrogen bonding HSP of about 5.4 MPa$^{0.5}$. Thus, the solvent system of 2,6-dimethylpyridine has an Ra with respect to PIB-PUR of about 5.2 and an RED of about 0.88.

As noted above, suitable solvent systems may not interfere with the polymerization process. That is, the solvent system is non-reactive with the polyisobutylene diol, the diisocyanate, the chain extender, or the optional polyether diol. Thus, the single solvent component, or the plurality of solvent components, of the solvent system do not include proton donating groups or any species that will react with alcohols. In some embodiments, the single solvent component, or the plurality of solvent components, of the solvent system do not include hydroxyl groups, acids, acid halides, primary amines, secondary amines, primary amides, or secondary amides. For example, a solvent system consisting of 2,6-dimethylpyridine does not include hydroxyl groups, acids, acid halides, primary amines, secondary amines, primary am ides, or secondary am ides.

Suitable solvent systems are also sufficiently volatile to evaporate from the PIB-PUR solution under conditions that will not damage the PIB-PUR. One indication of the volatility of a liquid is the Relative Evaporation Rate (RER). As used herein, the RER is the rate of evaporation of a liquid relative to the rate of evaporation of N-butyl acetate, in which the evaporation rate of N-butyl acetate is 100. In some embodiments, the single solvent component, or the plurality of solvent components, of the solvent system with an RER greater than about 0.01, greater than about 0.1, greater than about 1, or greater than any value between any of the preceding values may have volatility sufficient to evaporate from the PIB-PUR solution.

Another indication of the volatility of a liquid is its boiling point under a pressure of 1 bar. In some embodiments, the single solvent component, or the plurality of solvent components, of the solvent system with a boiling point less than about 150° C., about 200° C., about 250° C., about 300° C., about 350° C., or less than any temperature between any of the preceding temperatures may have volatility sufficient to evaporate from the PIB-PUR solution.

Yet another indication of the volatility of a liquid is its vapor pressure. In some embodiments, the single solvent component, or the plurality of solvent components, of the solvent system with a vapor pressure at 25° C. of greater than about 0.5 millimeters of mercury (mm Hg), greater than about 1 mm Hg, greater than about 2 mm Hg, greater than about 3 mm Hg, greater than about 5 mm Hg, or greater than about 10 mm Hg, or greater than any vapor pressure between any of the preceding vapor pressures may have volatility sufficient to evaporate from the PIB-PUR solution.

In some embodiments, the single solvent component, or the plurality of solvent components, of the solvent system may have an RER greater than about 0.01, greater than about 0.1, or greater than about 1, or greater than any value between any of the preceding values; may have a boiling point less than about 150° C., about 200° C., about 250° C., about 300° C., about 350° C., or less than any temperature between any of the preceding temperatures, and may have a vapor pressure greater than about 0.5 mm Hg, greater than about 1 mm Hg, greater than about 2 mm Hg, greater than about 3 mm Hg, greater than about 5 mm Hg, or greater than about 10 mm Hg, or greater than any vapor pressure between any of the preceding vapor pressures. For example, a solvent system consisting of 2,6-dimethylpyridine has an RER of about 17, a boiling point of about 144° C. at 1 bar, and a vapor pressure of 3.4 mm Hg at 25° C.

As noted above, embodiments in which solvent-based deposition processes employ electric fields to control the deposition of the PIB-PUR solution, such as electrospinning and electrospraying, suitable solvent systems also have polarity and hydrogen bonding levels sufficient to support interaction between the PIB-PUR solution and the electric fields. In such embodiments, a suitable solvent system may include a solvent component having a polar HSP of at least about 5.0 MPa$^{0.5}$, about 5.6 MPa$^{0.5}$, about 6.2 MPa$^{0.5}$, about 6.8 MPa$^{0.5}$, or about 7.4 MPa$^{0.5}$, and a hydrogen bonding HSP of at least about 4.4 MPa$^{0.5}$, about 4.6 MPa$^{0.5}$, about 4.8 MPa$^{0.5}$, about 5.0 MPa$^{0.5}$, or about 5.2 MPa$^{0.5}$. In other embodiments, in which the solvent-based deposition process employs electric fields to control the deposition of the PIB-PUR solution, a suitable solvent system may include at least one solvent component having a polar HSP of at least about 5.0 MPa$^{0.5}$, about 5.6 MPa$^{0.5}$, about 6.2 MPa$^{0.5}$, about 6.8 MPa$^{0.5}$, or about 7.4 MPa$^{0.5}$, and at least one other solvent component having a hydrogen bonding HSP of at least about 4.4 MPa$^{0.5}$, about 4.6 MPa$^{0.5}$, about 4.8 MPa$^{0.5}$, about 5.0 MPa$^{0.5}$, or about 5.2 MPa$^{0.5}$. For example, a solvent system consisting of 2,6-dimethylpyridine has a polar HSP of about 8.9 MPa$^{0.5}$ and a hydrogen bonding HSP of about 5.4 MPa$^{0.5}$.

In some embodiments, the solvent system may consist of a single solvent component. In some embodiments, the single solvent component may be selected from a group consisting of 2,6-dimethylpyridine benzaldehyde, 1,3-dioxolane, butyl benzoate, methyl phenylacetate, benzyl methyl ketone, ethyl cinnamate, 1,4-dioxane, cyclohexanone, propiophenone, ethyl phenylacetate, methylene chloride, benzyl ethyl ketone, tetrahydrofuran, isophorone, N-methyl-2-pyrrolidone, glycerol triacetate, phenyl acetonitrile, N,N-dimethyl formamide, N,N-dimethyl acetamide, diabasic esters, and cyclopentyl methyl ether.

In other embodiments, the solvent system may include two solvent components, a first solvent component and a second solvent component. In some embodiments, the first solvent component may be benzaldehyde and second solvent component may include one of 1,3-dioxolane, 1,4-dioxane, glycerol triacetate, ethyl 3-ethoxypropionate, tetrahydrofuran, dimethyl sulfoxide, diabasic esters, tetramethylene sulfone, and methyl phenylacetate. In other embodiments, the first solvent component may be 1,3-dioxolane and the second solvent component may be one of caprolactone (epsilon), phenyl acetonitrile, and propylene carbonate. In still another embodiment, the first solvent component may be 1,4-dioxane and the second solvent component may be caprolactone (epsilon). In some embodiments, the first solvent component may be present in concentrations of greater than or equal to about 50 wt. %, with the balance being the second solvent component. In some embodiments, a weight ratio of the first solvent component to the second solvent component may be 50% to 50%, 60% to 40%, 70% to 30%, 80% to 20%, or 90% to 10%, or 96% to 4%, or any weight ratio between any of the preceding weight ratios.

In some other embodiments, the solvent system may include three solvent components, a first solvent component, a second component, and a third solvent component. In some embodiments, the first solvent component may be benzaldehyde, the second component may be 1,4-dioxane, and the third solvent component may be one of caprolactone (epsilon), dimethyl sulfoxide, tetramethylene sulfone, propylene carbonate, gamma-butyrolactone, and N-methyl-2-pyrrolidone. In other embodiments, the first solvent component may be 1,4-dioxane, the second component may be caprolactone (epsilon), and the third solvent component may be one of aromatic hydrocarbons, toluene, ethyl benzene, butyl benzoate, phenyl acetonitrile, and xylene. In some embodiments, the second solvent component may be present in as little as about 20 wt. %, about 25 wt. %, or about 30 wt. %, or may be as great as about 35 wt. %, about 40 wt. %, or about 45 wt. %, or between any pair of the foregoing values. For example, in some embodiments, the second solvent component may be present in an amount from about 20 wt. % to about 45 wt. %, about 25 wt. % to about 40 wt. %, or about 30 wt. % to about 35 wt. %. In some embodiments, the third solvent component may be present in an amount as little as about 2 wt. %, about 5 wt. %, about 10 wt. %, or about 20 wt. %; with the balance being the first solvent component.

The PIB-PUR solution may be deposited onto at least a portion of the medical electrical lead 10 by a solvent-based deposition process. In solvent-based deposition processes, a first portion of the solvent system may evaporate during deposition of the PIB-PUR solution. Once the PIB-PUR solution is deposited, a second portion of the solvent system may evaporate. Surprisingly, it was discovered that allophonate crosslinks form within the deposited PIB-PUR in situ during the evaporation of the second portion of the solvent system. The allophonate crosslinks form between the linear PIB-PUR segments. The additional structure provided by the allophonate crosslinks produces a PIB-PUR that may be stronger and more durable than PIB-PUR manufactured and deposited by previous methods. For example, in some embodiments, the resulting deposited PIB-PUR may be a thermoset polymer due to the allophonate crosslinking.

As described herein, PIB-PUR is maintained within the same solvent system from polymerization through deposition. That is, the polyisobutylene diol, the diisocyanate, the chain extender and the optional polyether diol, are polymerized in the same solvent system used for deposition of the polymerized PIB-PUR solution. Without wishing to be bound by any theory, it is believed that continuously maintaining the PIB-PUR in solution from polymerization through deposition supports continued reactivity of polymer chains within the PIB-PUR. In addition, polymerization may continue after the PIB-PUR solution is deposited. As the second portion of the solvent system evaporates, any of the polyisobutylene diol, the diisocyanate, the chain extender, and the optional polyether diol remaining in the PIB-PUR solution becomes more concentrated, leading to continued polymerization. The additional polymerization may produce a PIB-PUR that may be stronger and more durable than PIB-PUR manufactured and deposited by historical methods in which polymerization ends with the evaporation of solvent before the deposition process.

Figure 3:
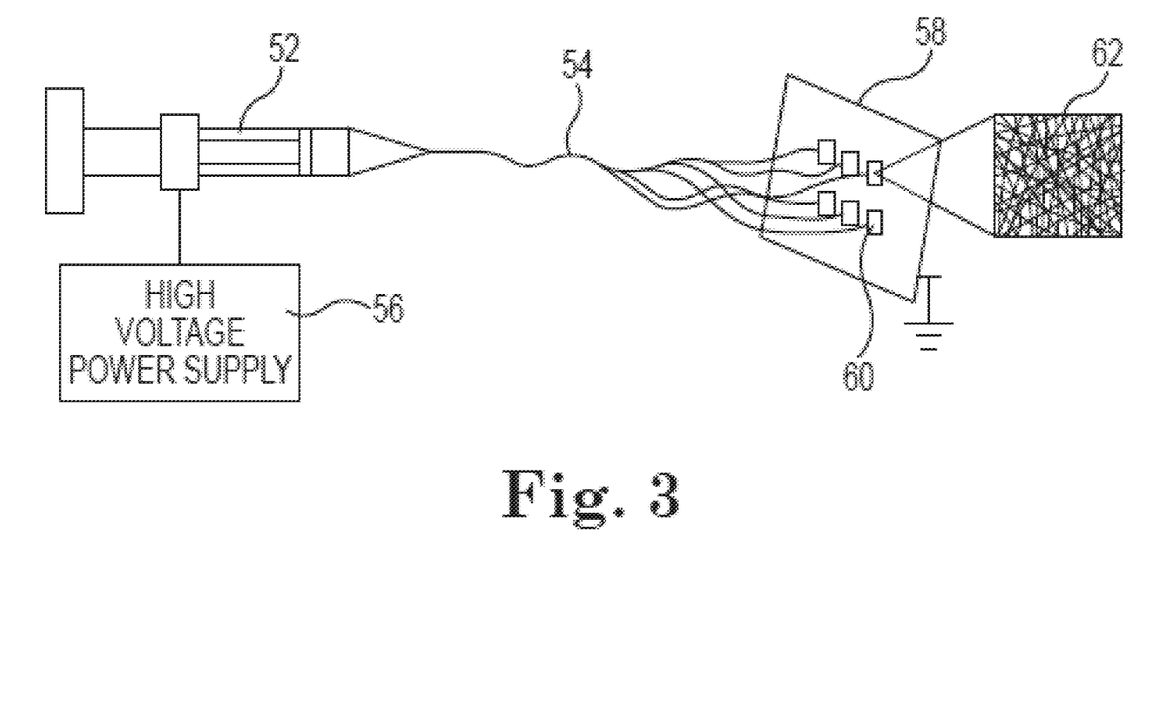
FIG. 3 is a schematic illustration of electrospinning.

FIG. 3 provides a schematic illustration of an exemplary solvent-based deposition process, electrospinning. An electric field may be used to draw a PIB-PUR solution 54 from a capillary source 52. The PIB-PUR solution 54 may be formed as described above in reference to FIGS. 2A and 2B employing a solvent system suitable for electrospinning as described above. In some embodiments, the capillary source 52 may be a syringe. The PIB-PUR solution 54 is drawn to a grounded collector 58. A high voltage power supply 56 may be used to power the process. The elements 60 to be coated, such as the insulative lead body 12 (FIGS. 1, 2A, and 2B), may be placed on the collector 58 to be coated. As the PIB-PUR solution 54 is drawn from the capillary source 52 toward the collector 58 to the elements 60, a surface area of the PIB-PUR increases substantially, leading to evaporation of the first portion of the solvent system from the PIB-PUR solution 54 during the deposition process. Once deposited, the second portion of the solvent system evaporates from the PIB-PUR solution 54 as polymerization continues and the allophonate crosslinks form within the deposited PIB-PUR, as described above. Upon drying, a thin polymeric web 62 of nanofibers may be formed. In some embodiments, the nanofiber sizes may be controlled by adjusting the relative concentration of polymer in the PIB-PUR solution 54.

Although the description herein discusses the PIB-PUR layer 40 deposited on the medical electrical lead 10, the PIB-PUR layer 40 may be deposited on any medical device such as, but not limited to, implantable electrical stimulation or diagnostic systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, and cardiac systems including implantable cardiac rhythm management (CRM) systems, implantable cardioverter-defibrillators (ICD's), and cardiac resynchronization and defibrillation (CRDT) devices, among others; and catheters.

EXAMPLES

The present invention is more particularly described in the following examples that are intended as illustrations only, since numerous modifications and variations within the scope of the present invention will be apparent to those of skill in the art. Unless otherwise noted, all parts, percentages, and ratios reported in the following examples are on a weight bases, and all reagents used in the examples were obtained, or are available, from the chemical suppliers described below, or may be synthesized by conventional techniques.

Example 1

Polymerizing PIB-PUR in 2,6-dimethylpyridine

A mixture of 14.3 g of polyisobutylene diol (saturated, 88.8% polyisobutylene) and 6.82 g of polytetramethylene oxide diol was initially combined with 50 g of toluene. The mixture was heated overnight under a nitrogen purge at a temperature of 70° C. to remove moisture and toluene. The mixture was added to a 100 ml glass reactor along with 8.57 g of methylenediphenyl diisocyanate and 65 g of 2,6-dimethylpyridine. The mixture was agitated at 150 RPM and maintained at a temperature of 90° C. Agitation was provided by a rotating polytetrafluoroethylene paddle. After two hours, 0.02 g of tin(II) 2-ethylhexanoate with 3 ml of toluene was added to the reactor. After five minutes, 1.94 g of 1,4-butanediol was slowly added to the reactor along with an additional 25 g of 2,6-dimethylpyridine to prevent the solution from becoming too viscous as the reactants polymerized to form PIB-PUR in solution with the 2,6-dimethylpyridine. After one hour, the PIB-PUR solution was ready to be employed in a solvent-based deposition process.

Example 2

Depositing PIB-PUR in 2,6-dimethylpyridine by Electrospinning

Figure 4:
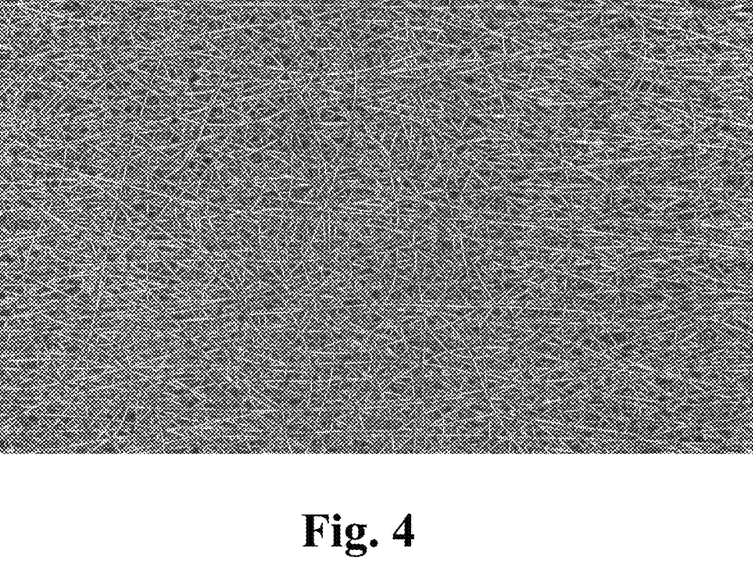
FIG. 4 is an image of a thin polymeric web of polyisobutylene-polyurethane block copolymer formed on an electrode coil of a lead in accordance with embodiments of the present invention.

Lithium bromide salt (LiBr) was combined with the mixture of the PIB-PUR solution prepared as described above in Example 1 to form a solution containing 0.1 weight percent LiBr. The PIB-PUR solution/salt mixture was loaded into a syringe and connected to a nozzle of an electrospinning machine. The PIB-PUR solution/salt mixture was electrospun at a flow rate of 0.3 milliliters per hour onto an electrode coil of a medical electrical lead positioned 10 cm from a tip of the nozzle to form a polymeric web on the electrode coil. Ambient conditions included a relative humidity of 34% and a temperature of 23° C. FIG. 4 is an image of the resulting thin polymeric web of PIB-PUR magnified 1000 times.

Example 3

Depositing PIB-PUR in 2,6-dimethylpyridine by Spray Coating

A mixture of 69.795 g of the PIB-PUR solution prepared as described in Example 1 and an additional 75 ml of 2,6-dimethylpyridine was processed in a centrifuge for 20 minutes at 5000 RPM to dilute the PIB-PUR solution, reducing the viscosity from 0.354 Pa s to 0.048 Pa s. The PIB-PUR content measured 26.6% before dilution and 15.2% after dilution. The diluted PIB-PUR solution was loaded into a DAGR® Gravity Air brush and sprayed onto a braided inner coil for a medical electrical lead. The coil was disposed on a mandrel rotating at 350 RPM at room temperature and 60.2% relative humidity.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for making an implantable medical device including a polyisobutylene-polyurethane block copolymer, the method comprising:
    polymerizing a polyisobutylene diol, a diisocyanate, a chain extender, and optionally a polyether diol, in a solvent system to form a polyisobutylene-polyurethane block copolymer solution;
    depositing the polyisobutylene-polyurethane block copolymer solution onto at least a portion of the implantable medical device; and
    evaporating the solvent system from the deposited polyisobutylene-polyurethane block copolymer solution wherein the solvent system includes one or more solvents components present during the polymerization step and the depositing step.

2. The method of claim 1, wherein evaporating the solvent system includes:
    evaporating a first portion of the solvent system while depositing the polyisobutylene-polyurethane block copolymer solution; and
    evaporating a second portion of the solvent system following deposition of the deposited polyisobutylene-polyurethane block copolymer solution.

3. The method of claim 2, wherein allophanate crosslinks form within the polyisobutylene-polyurethane block copolymer during evaporation of the second portion of the solvent system.

4. The method of claim 1, wherein the polymerization continues after deposition of the polyisobutylene-polyurethane block copolymer during evaporation of the solvent system.

5. The method of claim 1, wherein the solvent system consists of one or more solvent components, wherein the one or more solvent components have boiling points less than about 350° C., relative evaporation rates greater than about 0.01, and vapor pressures greater than about 0.5 mm Hg.

6. The method of claim 1, wherein the solvent system consists of one or more solvent components, and the one or more solvent components do not include hydroxyl groups, acids, acid halides, primary amines, secondary amines, primary amides, or secondary amides.

7. The method of claim 1, wherein the solvent system includes 2,6-dimethylpyridine.

8. The method of claim 7, wherein the solvent system consists of 2,6-dimethylpyridine.

9. The method of claim 1, wherein the solvent system includes benzaldehyde and a solvent component selected from the group consisting of 1,3-dioxolane, 1,4-dioxane, glycerol triacetate, ethyl 3-ethoxypropionate, tetrahydrofuran, dimethyl sulfoxide, diabasic esters, tetramethylene sulfone, and methyl phenylacetate.

10. The method of claim 1, wherein the solvent system includes benzaldehyde, 1,4-dioxane, and a solvent component selected from the group consisting of caprolactone (epsilon), dimethyl sulfoxide, tetramethylene sulfone, propylene carbonate, gamma-butyrolactone, and N-methyl-2-pyrrolidone.

11. The method of claim 1, wherein the polymerizing the polyisobutylene diol, the diisocyanate, the chain extender, and optionally the polyether diol, within the solvent system includes adding a tin catalyst to the solvent system.

12. The method of claim 1, wherein depositing includes at least one of solvent casting, spray coating, or dip coating the polyisobutylene-polyurethane block copolymer solution onto the implantable medical device.

13. The method of claim 1, wherein the solvent system includes:
 a solvent component having a polar Hansen Solubility Parameter of at least about 5.0 MPa$^{0.5}$ and a hydrogen bonding Hansen Solubility Parameter of at least about 4.4 MPa$^{0.5}$; or
 at least one solvent component having a polar Hansen Solubility Parameter of at least about 5.0 MPa$^{0.5}$ and at least one other solvent component having a hydrogen bonding Hansen Solubility Parameter of at least about 4.4 MPa$^{0.5}$.

14. The method of claim 13, wherein depositing includes at least one of electrospinning and electrospraying the polyisobutylene-polyurethane block copolymer solution onto the implantable medical device.

15. The method of claim 1, wherein the diisocyanate is 4,4'-methylenediphenyl diisocyanate, the chain extender is 1,4-butanediol, and the optional the polyether diol is polytetramethylene oxide diol.

16. The method of claim 1, wherein a Hansen Solubility Parameter Distance Relative Energy Difference between the polyisobutylene-polyurethane block copolymer and the solvent system is less than about 1.

17. The method of claim 1, wherein the solvent system is not evaporated from the polyisobutylene-polyurethane solution between the polymerization and the deposition steps.

18. An implantable medical lead including a polyisobutylene-polyurethane block copolymer, the copolymer comprising:
 a plurality of linear polyisobutylene-polyurethane block copolymer segments; and
 a plurality of allophanate crosslinks between the linear polyisobutylene-polyurethane block copolymer segments, wherein the polyisobutylene-polyurethane block copolymer is in the form of a plurality of electrospun fibers on a surface of the medical lead.

19. The device of claim 18, wherein the copolymer is a thermoset polymer.

* * * * *